(12) United States Patent
Shepard

(10) Patent No.: US 7,083,327 B1
(45) Date of Patent: Aug. 1, 2006

(54) METHOD AND APPARATUS FOR DETECTING KISSING UNBOND DEFECTS

(75) Inventor: Steven M. Shepard, Southfield, MI (US)

(73) Assignee: Thermal Wave Imaging, Inc., Ferndale, MI (US)

( * ) Notice: Subject to any disclaimer, the term of this patent is extended or adjusted under 35 U.S.C. 154(b) by 0 days.

(21) Appl. No.: 09/453,319

(22) Filed: Dec. 2, 1999

Related U.S. Application Data

(60) Provisional application No. 60/128,031, filed on Apr. 6, 1999.

(51) Int. Cl.
G01N 25/72 (2006.01)
G01N 3/00 (2006.01)
G01J 5/10 (2006.01)

(52) U.S. Cl. ............... 374/46; 374/5; 374/57; 374/124; 73/150 A; 702/34; 702/40

(58) Field of Classification Search ............. 374/4, 374/5, 6, 7, 45, 50, 124, 55, 43, 57, 49; 73/598.5, 73/150 R, 150 A, 799, 827
See application file for complete search history.

(56) References Cited

U.S. PATENT DOCUMENTS

| | | | | |
|---|---|---|---|---|
| 3,599,476 A | * | 8/1971 | Corbett | 73/15.6 |
| 3,681,970 A | * | 8/1972 | Wells | 73/15.4 |
| 3,698,234 A | * | 10/1972 | Allinikov | 73/15 |
| 3,744,295 A | * | 7/1973 | Allinikov | 73/15 R |
| 4,232,554 A | * | 11/1980 | Aleck | 73/577 |
| 4,289,030 A | * | 9/1981 | Alers et al. | 73/588 |
| 4,521,118 A | * | 6/1985 | Rosencwaig | 374/5 |
| 4,578,584 A | * | 3/1986 | Baumann et al. | 250/341.4 |
| 4,589,783 A | * | 5/1986 | Thomas et al. | 374/45 |
| 4,702,594 A | * | 10/1987 | Grant | 356/35.5 |
| 4,752,140 A | * | 6/1988 | Cielo et al. | 374/55 |
| 4,803,884 A | * | 2/1989 | Kaneta et al. | 73/598 |
| 4,860,687 A | * | 8/1989 | Frijlink | 118/500 |
| 4,866,276 A | * | 9/1989 | Leavens et al. | 250/341 |
| 5,032,727 A | * | 7/1991 | Cox, Jr. et al. | 374/5 |
| 5,111,048 A | * | 5/1992 | Devitt et al. | 250/342 |
| 5,201,841 A | * | 4/1993 | Lebeau et al. | 374/5 |
| 5,246,291 A | * | 9/1993 | Lebeau et al. | 374/5 |

(Continued)

FOREIGN PATENT DOCUMENTS

EP 535881 4/1993

(Continued)

OTHER PUBLICATIONS

Thermal and Infrared Methods For Nondestructive Testing of Adhesive-Bonded Structures, Kutzscher et al. Jul. 1968.*

(Continued)

*Primary Examiner*—Gail Verbitsky
(74) *Attorney, Agent, or Firm*—Honigman Miller Schwartz and Cohn LLP

(57) ABSTRACT

A active thermographic method for detecting subsurface defects in a specimen, particularly kissing unbond defects, includes heating a specimen, applying a force to the surface of the specimen to shift and separate the walls of the defect, and obtaining thermographic images of the specimen over time to monitor the heat flow through the specimen and detect thermal discontinuities. Because kissing unbond defects normally have good physical contact, and therefore good thermal conductivity, between its walls, these defects can go undetected in conventional active thermographic methods. By distorting the surface of the specimen, the kissing unbond defect is enlarged enough to generate sufficient thermal contrast for the defect to appear in the thermographic images.

28 Claims, 6 Drawing Sheets

U.S. PATENT DOCUMENTS

| | | | |
|---|---|---|---|
| 5,250,809 A * | 10/1993 | Nakata et al. | 250/330 |
| 5,270,809 A | 12/1993 | Gammie et al. | |
| 5,396,068 A * | 3/1995 | Bethea | 250/330 |
| 5,406,082 A * | 4/1995 | Pearson et al. | 250/339.01 |
| 5,407,275 A * | 4/1995 | Long | 374/5 |
| 5,562,345 A * | 10/1996 | Heyman et al. | 374/5 |
| 5,587,532 A * | 12/1996 | Rose | 73/579 |
| 5,709,469 A * | 1/1998 | Shearer et al. | 73/618 |
| 5,834,661 A * | 11/1998 | Nonaka et al. | 73/866 |
| 5,902,935 A * | 5/1999 | Georgeson et al. | 73/801 |
| 6,000,844 A * | 12/1999 | Cramer et al. | 374/5 |
| 6,175,416 B1 * | 1/2001 | Maris et al. | 356/381 |
| 6,200,022 B1 * | 3/2001 | Hammiche et al. | 374/46 |
| 6,236,049 B1 * | 5/2001 | Thomas et al. | 250/341.6 |
| 6,286,206 B1 * | 9/2001 | Li | 29/840 |
| 6,437,334 B1 * | 8/2002 | Thomas et al. | 250/341.6 |
| 6,759,659 B1 * | 7/2004 | Thomas et al. | 250/341.6 |
| 6,829,559 B1 * | 12/2004 | Bultman et al. | 702/155 |
| 6,880,379 B1 * | 4/2005 | Hedberg et al. | 73/12.01 |
| 2003/0106376 A1 * | 6/2003 | Shirzad et al. | 73/606 |
| 2004/0051035 A1 * | 3/2004 | Zombo et al. | 250/252.1 |
| 2004/0073398 A1 * | 4/2004 | Nikoonahad et al. | 702/155 |
| 2004/0074293 A1 * | 4/2004 | Pundt et al. | 73/150 A |
| 2004/0089811 A1 * | 5/2004 | Lewis et al. | 250/341.6 |
| 2004/0089812 A1 * | 5/2004 | Favro et al. | 250/341.6 |
| 2005/0008215 A1 * | 1/2005 | Shepard | 382/141 |
| 2005/0167596 A1 * | 8/2005 | Rothenfusser et al. | 250/341.6 |

FOREIGN PATENT DOCUMENTS

| | | | | |
|---|---|---|---|---|
| GB | 2164147 A | * | 3/1986 | 374/4 |
| GB | 2168494 A | * | 6/1986 | 374/5 |
| JP | 0151046 | * | 8/1984 | 374/4 |
| SU | 0565239 | * | 7/1977 | 374/5 |
| SU | 1081510 | * | 3/1984 | 374/4 |
| SU | 1081510 A | * | 3/1984 | |
| SU | 1198423 | * | 12/1985 | 374/5 |
| SU | 0879452 | * | 3/1986 | 374/50 |

OTHER PUBLICATIONS

Thermal Bond Inspection System, Technical References E. Cramer, NASA, 1993.*

Thermography and Ultrasonics Find Flaws in Composites, Langley Research Center, Sep. 1993.*

H.I.McHenry. A Compliance Method for Crack Growth Studies at Elevated Temperature. Journal of Materials, JMLSA, vol. 6, No. 4, pp. 862-873, Dec. 1971.*

NN82102633. IBM Tschnical Disclosure Bulletin. Pyroelectric Thermal Diffusion Microscope. Oct. 1982.*

Thermography and Ultrasonics Find Flaws in Composites, Laser Tech Brief, vol. 1, No. 1, Sep. 1993.

* cited by examiner

METHOD AND APPARATUS FOR DETECTING KISSING UNBOND DEFECTS

This application claims the benefit of U.S. Provisional Application No. 60/128,031 filed Apr. 6, 1999.

TECHNICAL FIELD

The present invention is directed to a method and apparatus for detecting subsurface defects in a specimen, and more particularly to a method and apparatus for detecting kissing unbond defects.

BACKGROUND ART

Active thermographic methods are often used to detect subsurface defects in a test specimen; that is, defects that are not readily ascertainable by viewing the specimen's surface. Active thermographic methods are often preferred because they are non-destructive and because they are capable of quickly locating subsurface defects over a large surface area. These methods usually involve heating the surface of the specimen and monitoring the subsequent heat signature radiated over a period of time from the specimen by way of an infrared camera. Subsurface air gaps or vacuums within the tested specimen are good thermal insulators when compared with the surrounding material and will therefore appear as a high-contrast thermal discontinuity in the thermographic image sequence due to the differences in heat flow between the defect and the surrounding defect-free area.

In some cases, however, the subsurface defect does not appear clearly in the thermographic image sequence because the walls of the defect are in mechanical contact, allowing at least some heat flow across the defect. This type of defect is often called a "kissing unbond" defect and is illustrated in FIG. 1A. As can be seen in FIG. 1A, the upper 106 and lower 108 walls of the defect 100 touch each other. Conventional active thermographic methods often cannot detect this type of defect because the mechanical contact between the walls of the defect provides partial thermal conduction rather than a large thermal discontinuity, thereby decreasing the thermal contrast in the thermographic images. This sometimes occurs in bonded or laminated structures, where unbonded, partially bonded, or delaminated areas in the joint may appear completely bonded in the thermographic image sequence.

There is a need for a device and method that can detect a kissing unbond subsurface defect in a non-destructive manner via active thermographic techniques.

SUMMARY OF THE INVENTION

Accordingly, the present invention detects a kissing unbond-type subsurface defect in a specimen by changing the dimensions of the defect while or immediately after the part is heated. The specimen's surface temperature is monitored over time to detect the defect. More particularly, the invention includes an image generator, such as an infrared camera, and means for changing the pressure on a surface of the specimen being tested to stress and unstress the specimen. The pressure changes cause the walls of the kissing unbond defect to move relative to each other, separating and/or shifting the walls of the defect to create thermal discontinuities in the specimen and increase the thermal contrast between the defect and the surrounding material. The pressure changes can include applying a vacuum to generate a tensile force on the surface of the specimen, which displaces the specimen surface at areas containing kissing unbond defects, or applying acoustic, ultrasonic, or mechanical energy at selected time intervals to shift unbonded surface with respect to each other. As the degree of contact in the defect's walls is altered, sequential thermographic images of the sample are obtained over time as heat flows through the specimen, revealing defects that may otherwise be undetectable by conventional means.

DETAILED DESCRIPTION OF THE PREFERRED EMBODIMENTS

Figure 1A:
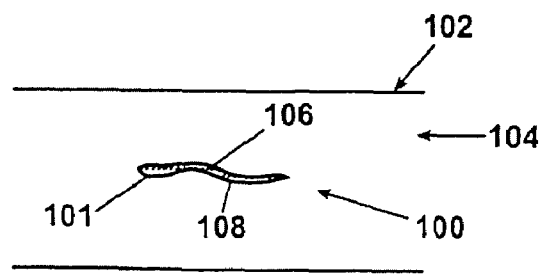
FIGS. 1A, 1B and 1C illustrate a kissing unbond defect and its corresponding temperature vs. time trace before and during application of a tensile force on a specimen's surface above the defect.
Figure 1B:
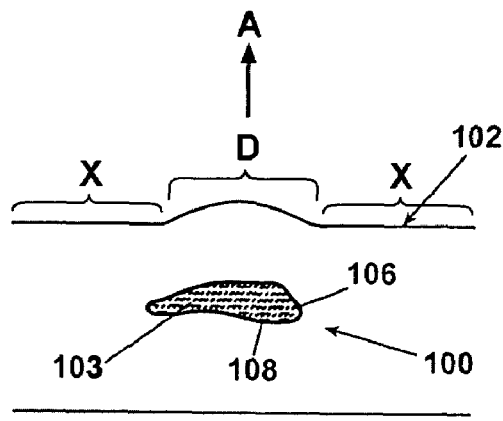

FIGS. 1A and 1B illustrate a kissing unbond defect 100 before and during application of a tensile force on a surface 102 of a specimen 104 to be tested. As explained above and as shown in FIG. 1A, the walls of the kissing unbond defect 100 may allow partial transfer of heat across the defect 100, causing marginal thermal contrast with respect to the surrounding material and rendering the defect 100 virtually undetectable via conventional methods.

FIG. 1B illustrates what happens to the kissing unbond defect 100 when tensile force is applied to the specimen surface 102 directly above the defect 100 generally in the direction of the arrow, A. If there is no defect in the area where the tensile force is applied, the tensile force causes little or no surface displacement, as indicated generally in the area of the surface 102 at reference numeral, X. If, however, the tensile force is applied to the surface 102 directly above a defect 100, as shown in FIG. 1B, the force will create a noticeable surface displacement in the direction of the arrow, A, as indicated generally in the area of the surface 102 at reference numeral, D, as the walls 106, 108 of the defect 100, (which define gap 101 FIG. 1A), separate or otherwise change in their degree of contact, thereby creating a larger gap 103 having different thermal (i.e. heat flow) characteristics than the surrounding material in the specimen 104. Gap 101, 103 may be an air gap or a gap that encloses a vacuum. Referring to FIG. 1A and then to FIG. 1B, it can be seen that the evaluation of the specimen 104 includes varying the degree of contact between the walls 106, 108 of the kissing unbond defect 100 in a way that does not cause the walls 106, 108 to intersect the surface 102 of the specimen 104. By varying the degree of contact between the walls 106, 108, gap 101 is enlarged 103. Enlarged gap 103 exacerbates the heat flow characteristics of the defect thereby enhancing the detectability of the defect 100.

Figure 1C:
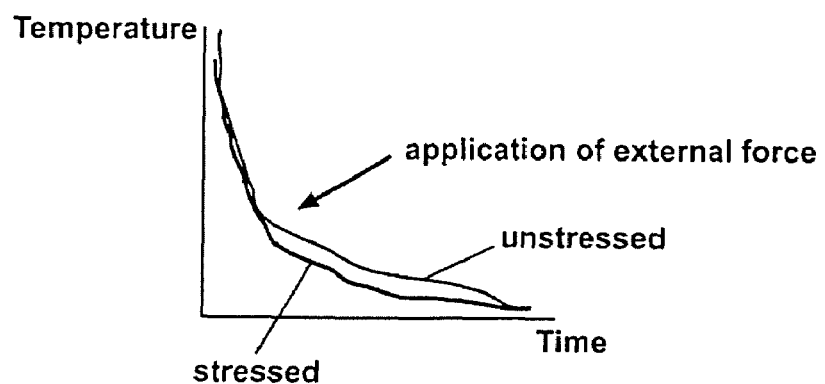

To detect thermal contrasts in the specimen 104 indicating the presence of a defect 100, one embodiment of the invention includes comparing the temperature vs. time trace of each pixel in the image of an unstressed specimen with the temperature vs. time trace of each pixel in the image of a stressed specimen. Any differences in the two traces, indicating a change in the dynamic heat flow characteristic in the stressed specimen as the specimen 104 cools, indicates the presence of a sub-surface defect. An example of such a comparison is illustrated in FIG. 1C, which illustrates a noticeable change in the temperature vs. time trace of the stressed specimen as force is applied. In this example, the sub-surface defect causes the specimen 100 to cool noticeably faster in the defect area than the unstressed sample over time. If the defect did not exist, the traces for both the stressed and the unstressed specimens would have been the same.

Figure 2:
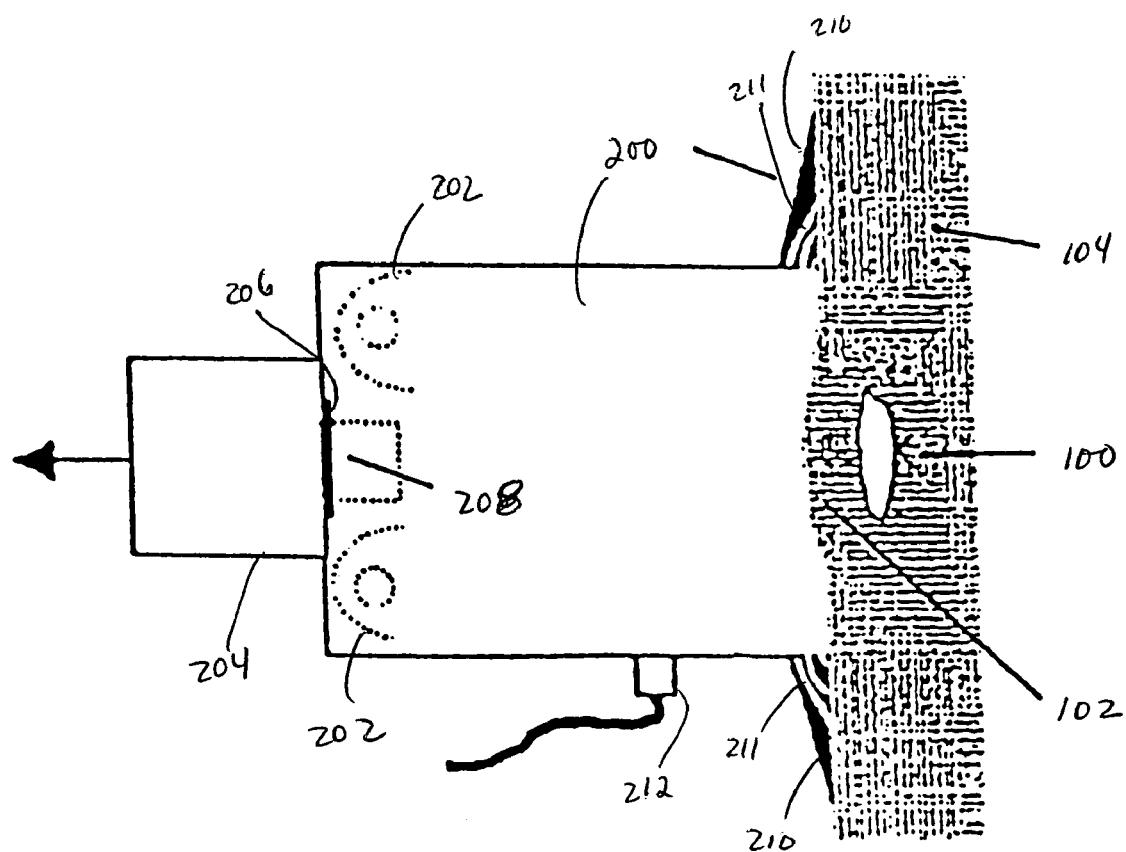
FIG. 2 illustrates a first embodiment of a kissing unbond defect detector according to the invention.

FIG. 2 illustrates one embodiment of the present invention. The apparatus shown in FIG. 2 includes a sealed enclosure 200, a heater, such as flashlamps 202, and an infrared camera 204. The enclosure should be sealed in an airtight manner so it can hold air pressure variations in a constant, measurable way. Although the figure shows that the enclosure 200 has an opening 206, preferably gasketed, for accommodating a lens 208 on the camera 204, the enclosure 200 can also be constructed with a window through which the lens 208 and/or the flashlamps 202 can project onto the specimen 104. Note that it is preferable to place the flashlamps 202 within the enclosure 200 since it may be difficult to find window materials that pass both infrared and visible wavelengths at acceptable levels for accurate monitoring. Possible window materials include zinc sulfide, zinc selenide, germanium, silicon, and any other material that is transparent in the wavelength band of the camera. The specific material chosen will depend on the infrared camera's 204 wavelength and the type of heater being used to heat the specimen. In short, the window material may be any material that is transparent in the wavelength band of the camera, has sufficient rigidity to withstand vacuum pressure, has the ability to withstand thermal cycling, and resists discoloration over time.

The sealed enclosure 200 preferably has a skirt 210 made out of a flexible material, such as rubber or an elastomeric polymer, to form a vacuum seal on the surface 102 of the specimen 104. The skirt 210 may also include holes 211 leading to the interior of the enclosure 200. A pump fitting 212 attached to the sealed enclosure 200 is connected to a pump (not shown) for increasing and decreasing the air pressure inside the enclosure 200.

To maintain the airtightness of the enclosure 200, all openings, such as the opening accommodating the infrared camera lens 208, should be sealed or fitted with gaskets. The pump can vary the air pressure inside the enclosure 200 by pumping air into or pulling air out of the enclosure 200, thereby distorting the surface 102 of the specimen 104 and shifting the walls of the kissing unbond defect 100. To detect a kissing unbond defect, the flashlamps 202 heat the surface 102 of the specimen 104, and the pump varies the pressure inside the enclosure 200 to vary the degree of contact between the walls 106, 108 of the kissing unbond defect 100, if one exists at the enclosure's 200 location.

The infrared camera 204 generates a series of thermographic images over time of the de-pressurized and/or pressurized images to capture information about the thermal energy flow through the specimen as the specimen 104 cools. As explained above with respect to FIGS. 1A and 1B, kissing unbond defects will tend to enlarge when the enclosure 200 is de-pressurized, thereby creating a thermal discontinuity, because the vacuum will distort the surface 102 above the defect 100 to a greater degree than the surface 102 of the material surrounding the defect 100. The thermographic image sequence generated by the camera 204 can be sent to a display monitor or computer (not shown) for further analysis, if desired. It is important to note that although the use of vacuum pressure is believed to be a preferred way to distort the surface 102, other techniques for distorting surface 102 are contemplated, such as physically loading the specimen (through tension, compression, shear, etc.) or vibrating the specimen (such as via ultrasonic means).

Figure 3:
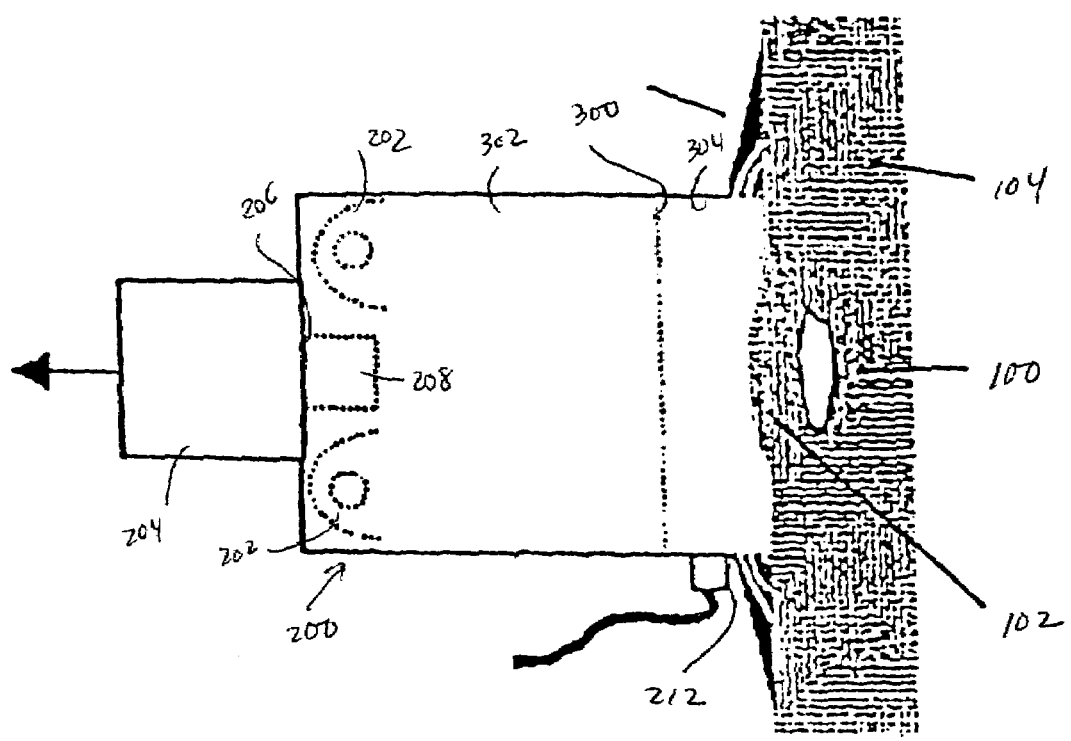
FIG. 3 illustrates a second embodiment of the inventive kissing unbond defect detector.

FIG. 3 illustrates a variation of the apparatus explained above by including an infrared transparent window 300 inside the enclosure 200, dividing the enclosure 200 into a first section 302 and a second section 304. The window 300 must create an airtight separation between the first and second sections 302, 304 so that the second section 304 can maintain variances in its air pressure. As in the first embodiment, the camera 204 and flashlamps 202 can be arranged outside the enclosure 200, or alternatively the camera lens 208 and/or the flashlamps 202 can be disposed inside the first section 302 of the enclosure 200, as illustrated in FIG. 3. The pump (not shown) is arranged to inject air into and/or withdraw air from only the second section 304 through the pump fitting 212, without varying the air pressure in the first section 302. De-pressurizing the second section 304 will pull on the surface of the specimen and shift the walls of any kissing unbond defects 100 below the surface, causing thermal contrast that is detectable by the infrared camera 204. In this embodiment, because the pump has to inject and remove air only from the second section 304 rather than from the entire enclosure 200, pressure changes can be conducted more quickly and with a smaller pump due to the reduced volume of the second section 304.

Figure 4:
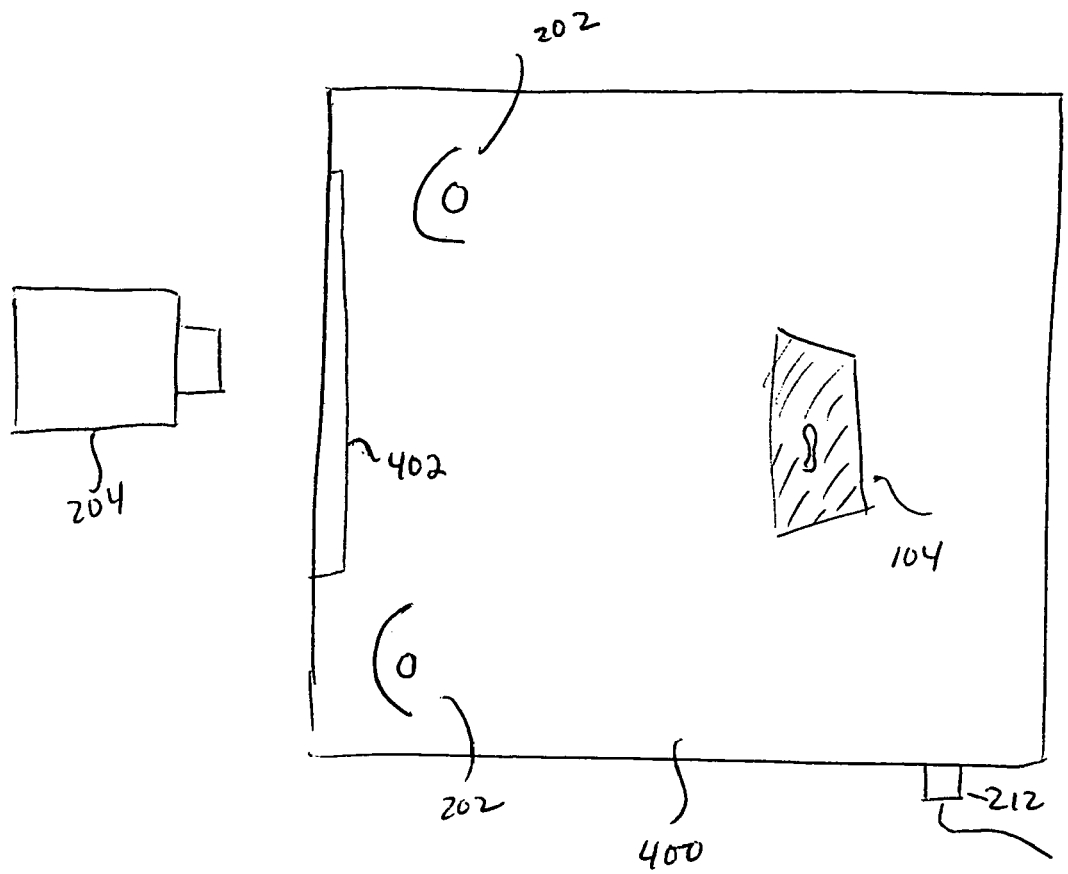
FIG. 4 illustrates a third embodiment of the inventive kissing unbond defect detector.

The devices shown in FIGS. 2 and 3 are particularly appropriate for evaluating smaller specimens 104 because the enclosure 200 only has to be moved a few times to cover the entire surface area of the specimen 104. For specimens having a larger surface area, however, individually testing small sections of the specimen 104 can be time-consuming because the enclosure 200 must be repositioned and re-pumped at each new location when the infrared camera 204 generates the thermographic image sequence for the new location. FIG. 4 illustrates another embodiment of the present invention where the pressure of the air surrounding the entire specimen 104 can be changed all at once rather than in individual small sections. The embodiment includes a sealed chamber 400 large enough to enclose the specimen 104. If the camera 204 and heater, such as a flashlamp 202, are both located inside the chamber 400, power cords and connectors can be run through gasketed ports (not shown) to the outside of the chamber 400 without compromising the airtightness of the chamber 400. Alternatively, as shown in FIG. 4, the chamber can include a transparent window 402 so that either the camera 204 or the flashlamps 202, or both, can be located outside the chamber 400. As explained above, the window 402 material is selected based on the camera wavelength and on the type of heater used. In this embodiment, the pump (not shown) pressurizes and/or de-pressurizes the entire chamber 400 via the pump fitting 212, thereby closing and/or opening all of the kissing unbond defects 100 in the specimen 104 at virtually the same time. Like the previously described embodiments, the flashlamps 202 heat the surface of the specimen before or during the pressure changes and the camera 204 generates active thermographic images to monitor the heat flow through the specimen 104. The specimen 104 and/or camera 204 can be repositioned to obtain thermographic image sequences for all surfaces of the specimen 104.

Figure 5A:
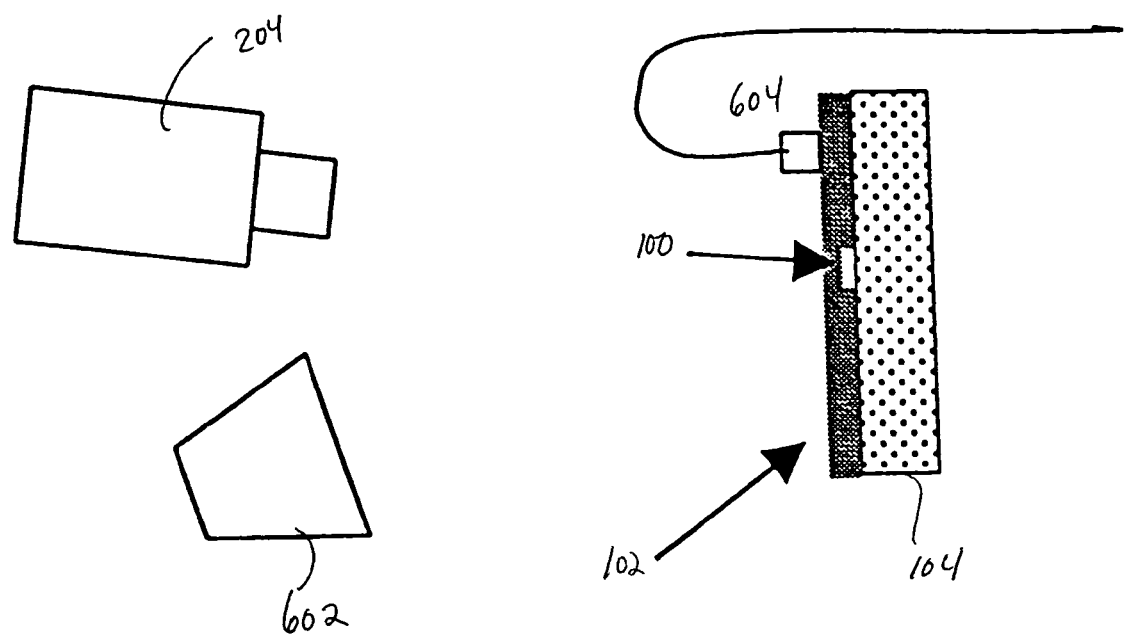
FIGS. 5A and 5B illustrate a fourth embodiment of the inventive kissing unbond defect detector.
Figure 5B:
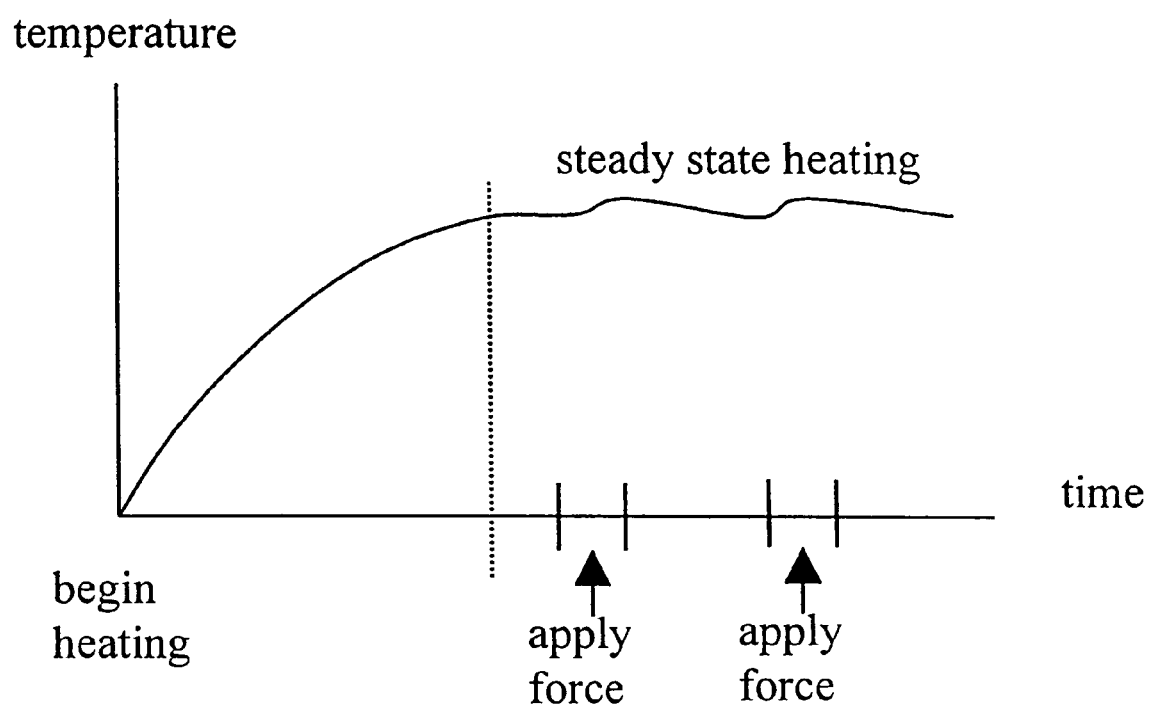
Figure 1A:
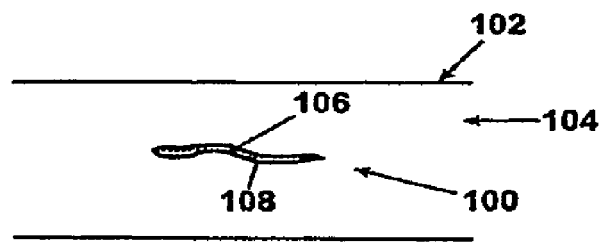
Figure 1B:
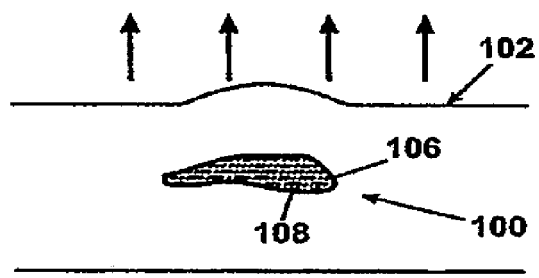
Figure 1C:
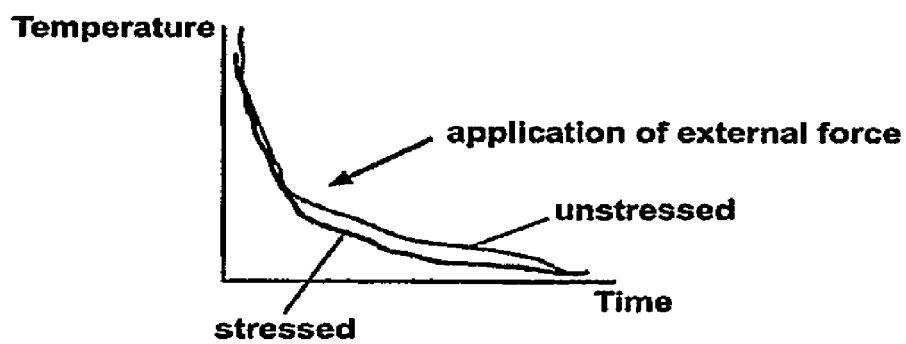
Figure 2:
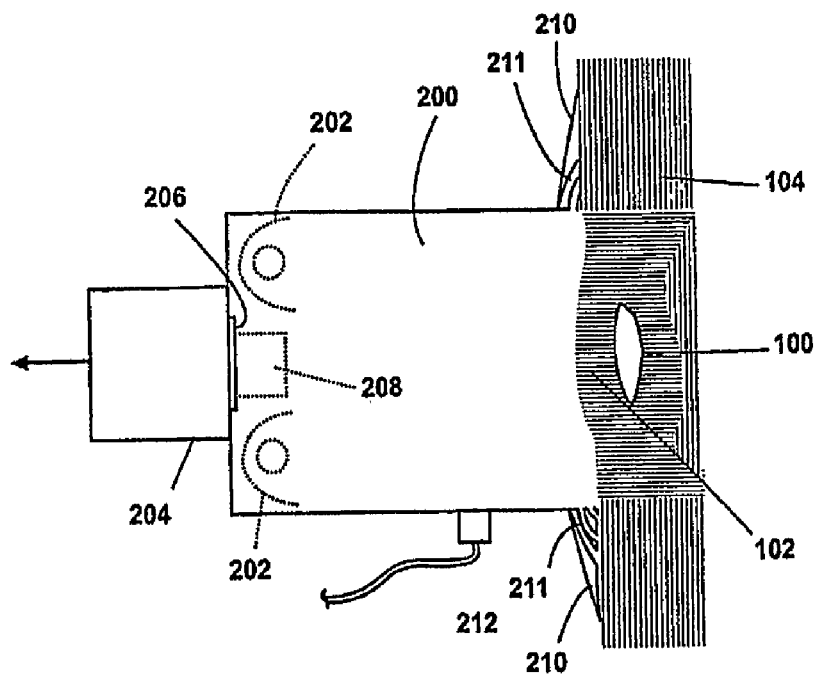
Figure 3:
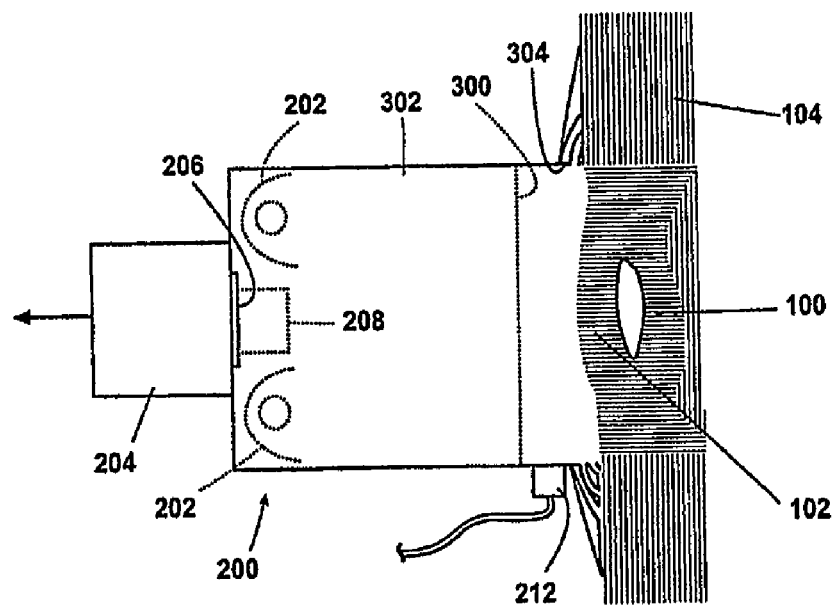
Figure 4:
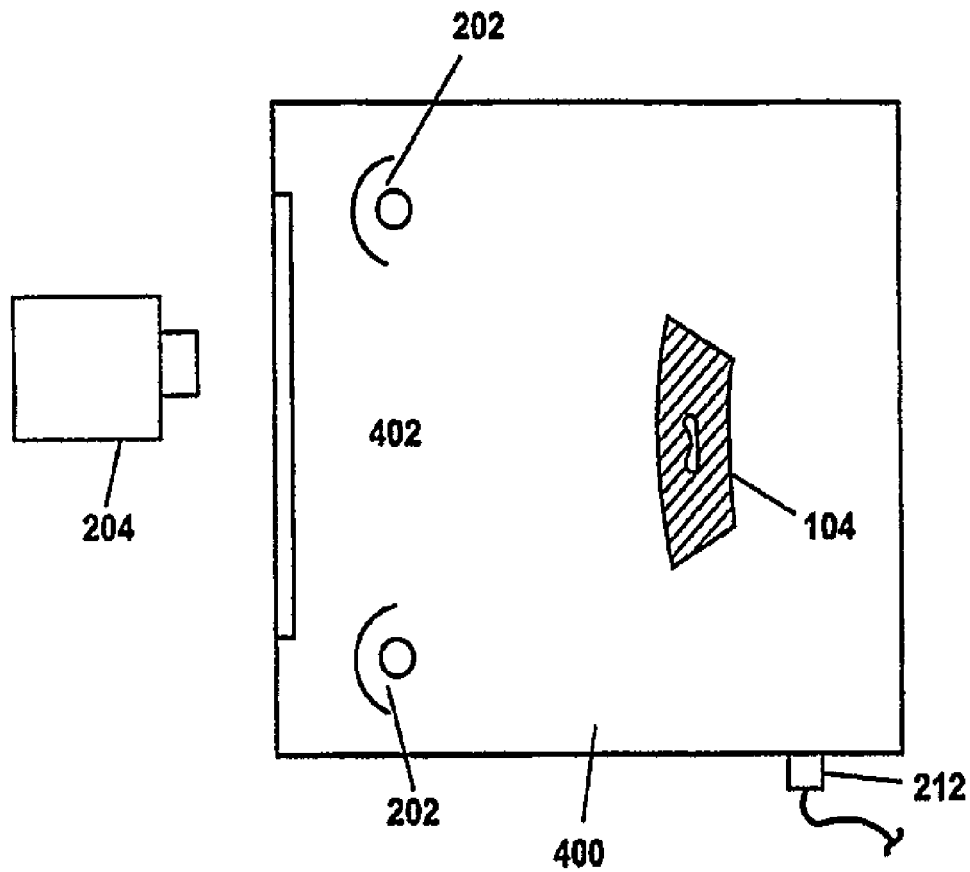
Figure 5A:
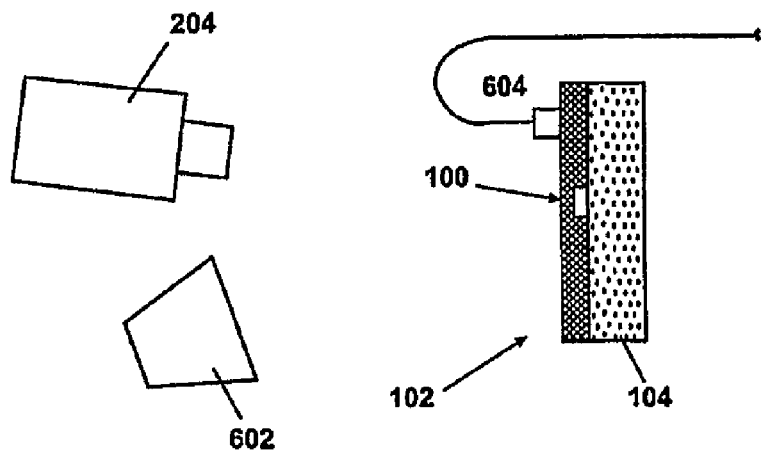
Figure 5B:
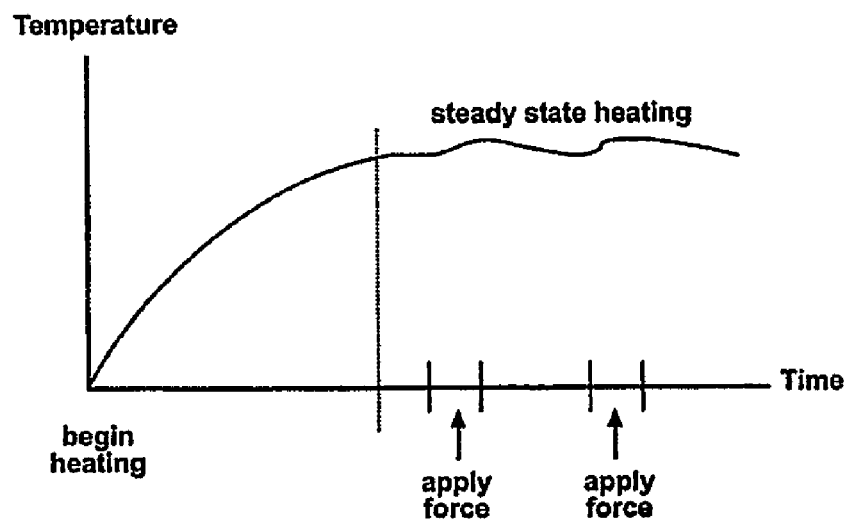

Yet another embodiment of the present invention is shown in FIGS. 5A and 5B. In this embodiment, heat is preferably provided by at least one low-power lamp 602 that continuously directs heat to the specimen surface 102. As a result, the surface temperature of the specimen 104 rises at a steady state or in a slow monotonic fashion while the specimen 104 is in an unstressed state. When the specimen 104 reaches a steady state temperature, the thermal energy from the lamps 602 is dissipated through the specimen 104 at the same rate that the energy is being absorbed. Further, for a sufficiently thick specimen 104, the specimen 104 will cool generally via smooth conduction of thermal energy from the surface being heated to the cooler rear portion of the specimen 104. Applying an external force to the specimen 104 will disrupt this equilibrium around the kissing unbond defect 100 and thereby generate sufficient thermal contrast for the defect 100 to be thermographically detectable. As illustrated in FIG. 5A, stressing the disbonded area can be conducted via ultrasound, acoustic, or mechanical energy through an attachment 604 coupled to the specimen's surface 102. Further, as can be seen in FIG. 6B, applying the external force in a discrete, systematic manner over time will create noticeable discontinuities in the temperature vs. time trace of the specimen 104 as the external force creates subsurface pockets that interrupt the flow of thermal energy through the specimen 104. The embodiment illustrated in FIGS. 5A and 5B is particularly suitable for inspecting coated metallic specimens, where the metallic specimen tends to be a better heat conductor than the coating. Any delaminations or weak bonding areas between the coating and the substrate tend to act as kissing unbond defects and can be stressed by the external force, making them detectable by the infrared camera 204.

Note that with all of the above disclosed embodiments, there are many ways and sequences in which to heat the specimen 104, vary the pressure on and around the specimen 104, and generate thermographic image sequences without departing from the scope of the invention. For example, the pump can generate a vacuum within the enclosure 200 or chamber 400, shifting the walls of any kissing unbond defects 100, before or during heating while the camera 204 generates a thermographic image sequence as the specimen 104 heats and cools. Alternatively, the kissing unbond defects 100 can be alternately stressed and unstressed by varying the pressure inside the enclosure 200 or chamber 400 or by starting and stopping force application and comparing the active thermographic images of the stressed specimen and the unstressed specimen. Thus, the invention can effectively detect kissing unbond defects 100 that would ordinarily go undetected by conventional active thermographic methods simply by displacing the surface 102 above the defect 100 to increase the thermal contrast between the defect 100 and the surrounding material. Further, the heat input can also be varied and sent in the form of a pulse, a step, modulated or continuously applied. The specific sequence in which the heating, stress application, and image generating steps are conducted does not matter in the invention as long as the stress changes at least one dimension of the kissing unbond defect to render it visible via active thermographic methods.

The manner in which the stressed image and the unstressed image are evaluated can be selected from various methods. Calculating/viewing the difference between the sums of the stressed images and the unstressed images is one way to compare the two images. Alternatively, histograms of the stressed and unstressed images can be compared, such as according to the method described in co-pending patent application Ser. No. 08/608,901 entitled "Method of Interpreting Thermographic Data For Non-Destructive Evaluation," incorporated herein by reference. Other methods include applying of a mathematical correlation function to correlate the two sets of images, viewing an image displaying the ratio between the stresses and unstressed images, and visually comparing the stressed and unstressed images without conducting additional calculations.

The application and removal of stress on the specimen can be repeated several times during a single heating cycle. Alternatively, separate heating cycles can be conducted when generating the stressed and unstressed images. Note that regardless of the specific method and device used to stress/unstress the specimen and monitor heat flow through the specimen, the methods and devices will reveal only kissing unbond defects because other defects that are detectable via conventional active thermographic methods will appear identical in the stressed and unstressed images and will therefore cancel each other out when the two images are compared.

It should be understood that various alternatives to the embodiments of the invention described herein may be employed in practicing the invention. It is intended that the following claims define the scope of the invention and that the method and apparatus within the scope of these claims and their equivalents be covered thereby.

What is claimed is:

1. A method for non-destructively evaluating a specimen for the presence of subsurface kissing unbond defects, comprising the steps of:

heating the specimen;

applying a non-destructive force to the specimen to vary a degree of contact between walls of said subsurface kissing unbond defect without causing said walls to intersect a surface of said specimen;

wherein the magnitude of the force used to vary the degree of contact between the walls is sufficient to disrupt a flow of thermal energy through said kissing unbond defect by exacerbating a thermal discontinuity associated with said kissing unbond defect; and generating an infrared image to detect the presence of a subsurface kissing unbond defect.

2. The method of claim 1, wherein the applying step includes decreasing air pressure in a vicinity of the specimen to change the at least one dimension of the subsurface defect.

3. The method of claim 1, wherein the applying step includes disturbing the specimen using ultrasonic, acoustic or mechanical energy.

4. The method of claim 1, wherein the applying step includes:

placing the specimen in a chamber; and generating a vacuum in the chamber to change at least one dimension of the subsurface defect.

5. The method of claim 1, wherein the applying step includes:

placing a sealed enclosure on the surface of the specimen; and generating a vacuum in the sealed enclosure to change the at least one dimension of the subsurface defect.

6. The method of claim 5, wherein the sealed enclosure is divided into two sections such that the vacuum generated in said vacuum generating step produces a vacuum in one of the two sections.

7. The method of claim 1, wherein said applying step includes increasing and decreasing the force on the specimen surface, wherein said image generating step includes generating a first thermographic image when the force is increased and generating a second thermographic image when the force is decreased, and wherein the method further comprises the step of comparing the first and second thermographic images to detect the subsurface defect.

8. The method of claim 7, wherein the image generating step generates a plurality of first thermographic images and a plurality of second thermographic images over time, and wherein the comparing step is conducted by calculating the difference of the sums of the first thermographic images and the second thermographic images.

9. The method of claim 7, wherein the image generating step generates a plurality of first thermographic images and a plurality of second thermographic images over time, and wherein the comparing step includes generating histograms corresponding to the plurality of first and second thermographic images and comparing the histograms for the plurality of first thermographic images with the histograms for the plurality of second thermographic images.

10. The method of claim 7, wherein the image generating step generates a plurality of first thermographic images and a plurality of second thermographic images over time, and wherein the comparing step includes mathematically correlating the plurality of first thermographic images with the plurality of second thermographic images.

11. The method of claim 7, wherein the image generating step generates a plurality of first thermographic images and a plurality of second thermographic images over time, and wherein the comparing step includes viewing an image corresponding to the ratio between the plurality of the first thermographic images and the plurality of the second thermographic images.

12. The method of claim 7, wherein the image generating step generates a plurality of first thermographic images and a plurality of second thermographic images over time, and wherein the comparing step includes visually comparing the plurality of first thermographic images and the plurality of second thermographic images.

13. The method of claim 7, wherein the applying step includes placing the specimen in a chamber before said image generating step.

14. The method of claim 7, wherein the applying step includes placing a sealed enclosure on the specimen surface before said image generating step.

15. A method for non-destructive evaluation of a specimen, comprising the steps of:
  heating the specimen;
  placing a sealed enclosure on a surface of the specimen;
  applying a non-destructive vacuum to at least a portion of the surface of the specimen by decreasing the air pressure in the sealed enclosure, wherein the vacuum from the applying step enlarges at least one dimension of the subsurface defect to create a thermal discontinuity; and
  generating an infrared image to detect the presence of a subsurface defect.

16. The method of claim 15, wherein the sealed enclosure is divided into two sections such that the vacuum generated in said applying step produces a vacuum in one of the two sections.

17. The method of claim 15, wherein said applying step further includes the step of increasing the air pressure in the sealed enclosure, wherein said generating step includes generating a first active thermographic image when the pressure is increased and generating a second active thermographic image when the pressure is decreased, and wherein the method further comprises the step of comparing the first and second active thermographic images to detect the subsurface defect.

18. An apparatus for non-destructively evaluating a specimen for detecting the presence of subsurface kissing unbond defects comprising:
  a heat-sensitive image generator that generates thermographic images;
  a heater that increases the temperature of the specimen; and
  means for applying a non-destructive force to the specimen, wherein the force applied by the applying means is sufficient to vary a degree of contact between walls of said subsurface kissing unbond defect without causing said walls to intersect a surface of said specimen thereby disrupting a flow of thermal energy through the specimen to exacerbate a thermal discontinuity within said specimen.

19. The apparatus of claim 18, wherein said heater is at least one flashlamp that directs heat to the specimen surface.

20. The apparatus of claim 18, wherein said applying means includes:
  a sealed enclosure that is placed on the specimen's surface; and
  a vacuum pump that generates a vacuum inside the sealed enclosure.

21. The apparatus of claim 20, wherein the sealed enclosure is divided into two sections, and wherein the vacuum pump generates the vacuum inside the sealed enclosure in one of the two sections.

22. The apparatus of claim 20, wherein the heater is a flashlamp disposed inside the sealed enclosure to direct light to the specimen surface.

23. The apparatus of claim 18, wherein said applying means includes:
  a chamber for holding the specimen; and
  a vacuum pump that generates a vacuum inside the chamber.

24. A method for non-destructively evaluating a specimen for the presence of kissing unbond defects, comprising the steps of:
  heating the specimen;
  applying a non-destructive force to the specimen, wherein the magnitude of the force is sufficient to vary a degree of contact between walls of said subsurface kissing unbond defect without causing said walls to intersect a surface of said specimen thereby disrupting a flow of thermal energy through the specimen to render a thermal discontinuity within said specimen ; and
  generating an infrared image to detect the presence of a subsurface kissing unbond defect, wherein the applying step includes disturbing the specimen using ultrasonic or acoustic energy.

25. The apparatus of claim 23, wherein the chamber includes a window, wherein the heater is a flashlamp located inside the chamber and directs light on the specimen to heat the specimen, and wherein at least part of the image generator is located outside the chamber.

26. The apparatus of claim 23, wherein at least one of the heater and the image generator are located inside the chamber.

27. The apparatus of claim 18, wherein said heater is a lamp that continuously directs heat to the specimen, and wherein said applying means includes an attachment that couples to the surface of the specimen to apply the force.

28. The apparatus of claim 27, wherein said attachment provides the force via ultrasonic, acoustic, or mechanical energy.

* * * * *

UNITED STATES PATENT AND TRADEMARK OFFICE
CERTIFICATE OF CORRECTION

| | | |
|---|---|---|
| PATENT NO. | : 7,083,327 B1 | |
| APPLICATION NO. | : 09/453319 | |
| DATED | : August 1, 2006 | |
| INVENTOR(S) | : Steven Shepard | |

It is certified that error appears in the above-identified patent and that said Letters Patent is hereby corrected as shown below:

In the Drawings:
Delete Figs. 1A-5B and replace with attached are four sheets of formal drawings replacing all Figures in this applications.

Signed and Sealed this

Tenth Day of April, 2007

JON W. DUDAS
*Director of the United States Patent and Trademark Office*